(12) United States Patent
    Zhang et al.

(10) Patent No.:    US 12,564,512 B2
(45) Date of Patent:       Mar. 3, 2026

(54) CONFIGURABLE BREATHING ASSIST MOUTHPIECE DEVICE

(71) Applicant: GOLDEN GALAXY CORPORATION, Henderson, NV (US)

(72) Inventors: Aaron Shijing Zhang, Boston, MA (US); Xinhang He, Parker, TX (US); Edison Xuanzhen Chen, Parker, TX (US); Lyucheng Cai, Houston, TX (US); Dillon Shiwei Zhang, Boston, MA (US); Mingyu Cui, Plano, TX (US); Bolin Miao, Durham, NC (US)

(73) Assignee: Golden Galaxy Corporation, Henderson, NV (US)

( * ) Notice: Subject to any disclaimer, the term of this patent is extended or adjusted under 35 U.S.C. 154(b) by 0 days.

(21) Appl. No.: 19/318,124

(22) Filed: Sep. 3, 2025

(65) Prior Publication Data

US 2026/0000534 A1      Jan. 1, 2026

Related U.S. Application Data

(63) Continuation-in-part of application No. 19/004,287, filed on Dec. 28, 2024, which is a continuation of
(Continued)

(51) Int. Cl.
    *A61F 5/56*          (2006.01)
    *A61F 5/05*          (2006.01)
(52) U.S. Cl.
    CPC ................ *A61F 5/566* (2013.01); *A61F 5/05* (2013.01)
(58) Field of Classification Search
    CPC ...... A61F 2005/563; A61F 5/566; A61F 5/56; A61C 7/08; A61C 7/36; A63B 2071/088; A63B 2071/086; A63B 71/085
    See application file for complete search history.

(56) References Cited

U.S. PATENT DOCUMENTS

| | | | | | |
|---|---|---|---|---|---|
| 4,457,708 | A | * | 7/1984 | Dufour | .................... A61C 7/00 |
| | | | | | 433/6 |
| 6,371,758 | B1 | * | 4/2002 | Kittelsen | .............. A63B 71/085 |
| | | | | | 128/861 |

(Continued)

OTHER PUBLICATIONS

Takai et al., "Maximum Bite Force Analysis in Different Age Groups," International Archives of Otorhinolaryngology vol. 18 No. Mar. 2014.

(Continued)

*Primary Examiner* — Camtu T Nguyen
(74) *Attorney, Agent, or Firm* — Stephen E. Zweig

(57) ABSTRACT

A mouthpiece device and method for helping human users with congested sinuses breathe freely through their mouths while sleeping while minimizing the risks of dry mouth and drooling. The device fits between the user's jaws and is configured to apply a gentle jaw and lip opening pressure sufficient to at least partially open a sleeping user's jaw and lips while the jaw and lip muscles are relaxed. At the same time, the device is configured to so that when the user, while still sleeping, activates their jaw or lip muscles to swallow, this action overcomes the gentle opening force, allowing the user to easily swallow without conscious effort. Methods of configuring the device shape and opening forces are also taught. These include using implanted sensors, processors, and actuators configured to optimize the opening forces according to user physiology; and/or wireless connection to external sensing and control devices.

20 Claims, 11 Drawing Sheets

Related U.S. Application Data application No. 18/793,574, filed on Aug. 2, 2024, now Pat. No. 12,193,966, which is a continuation-in-part of application No. 18/390,605, filed on Dec. 20, 2023, now abandoned, which is a continuation of application No. 18/449,539, filed on Aug. 14, 2023, now Pat. No. 11,850,117.

(56)                    References Cited

U.S. PATENT DOCUMENTS

| | | | | |
|---|---|---|---|---|
| 9,585,732 B2 * | 3/2017 | Piancino | ................. | A61F 5/566 |
| 2009/0159089 A1 * | 6/2009 | Jansheski | ................ | A61F 5/566 |
| | | | | 128/861 |

OTHER PUBLICATIONS

Brunton et al., "Estimation of jaw-opening forces in adults," Orthod, Craniofac. Res. 2017;1-6.

* cited by examiner

170u

154

170l

CONFIGURABLE BREATHING ASSIST MOUTHPIECE DEVICE

CROSS-REFERENCE TO RELATED APPLICATIONS

This application is a continuation in part of U.S. patent application Ser. No. 19/004,287, filed Dec. 28, 2024, application Ser. No. 19/004,287 is a continuation of U.S. patent application Ser. No. 18/793,574, filed Aug. 2, 2024, now U.S. Pat. No. 12,193,966, issued Jan. 14, 2025; application Ser. No. 18/793,574 was a continuation in part of U.S. patent application Ser. No. 18/390,605, filed Dec. 20, 2023; application Ser. No. 18/390,605 was a continuation of U.S. patent application Ser. No. 18/449,539, filed Aug. 14, 2023, now U.S. Pat. No. 11,850,117 issued Dec. 26, 2023; the entire contents of these applications are incorporated herein by reference.

BACKGROUND OF THE INVENTION

Field of the Invention

This invention is in the field of mouthpiece devices to help individuals suffering from clogged sinuses to breathe by mouth during sleep.

Description of the Related Art

Nighttime breathing appliances, such as CPAP devices, anti-snore devices and similar devices are commonly used to help individuals suffering from snoring, sleep apnea, and other breathing disorders breathe comfortably during their sleep.

Other types of mouth devices include various mouth inserts to help prevent teeth grinding during sleep. Still, other types of mouth devices, such as braces, can be used to slowly reposition the alignment of the user's teeth.

However, as allergy sufferers can attest, another type of sleep-breathing problem occurs when the individual's sinuses become blocked by inflammation or other cause. Nose breathing now becomes impossible, making breathing by mouth the only option. However, if the individual's mouth remains continually open, their mouth will dry out, and/or they will have trouble managing their saliva during sleep. This leads to difficulties in sleeping and excessive drying of the mouth tissues.

Prior art studies on the maximum amount of force exerted by human jaws at different ages include the work of Takai et al., International Archives of Otorhinolaryngology Vol. 18 No. 3/2014. Prior art studies on the minimum amount of force required to open human jaws include the work of Brunton et al., Orthod, Craniofac. Res. 2017; 1-6.

BRIEF SUMMARY OF THE INVENTION

The invention was inspired, in part, by the insight that what is needed is a new type of mouth device that operates to assist breathing while the user is asleep. This new type of device should fit between the user's jaws and apply a gentle jaw and lip opening pressure sufficient to at least partially open the user's jaw and lips when the user's jaw muscles and lip muscles are relaxed. At the same time, the pressure exerted by the device should be precisely calibrated so that when the still-sleeping user activates their jaw and lip muscles to swallow saliva, the device yields, allowing the user to close their jaws and lips without exerting conscious effort.

Such a device needs to adjust to the dimensions of an individual user's mouth and have a jaw and lip opening force adjusted to be just above the minimum opening force for that particular user. Here, we disclose both such an adjustable device and a method for adjusting the device to apply suitable jaw and opening force for a given user.

The invention was also inspired, in part, by the insight that this minimum opening force may vary according to the user's physiological state. Thus, methods to monitor the user's physiological state, as well as methods to dynamically adjust this opening force according to the user's physiological state, may also be useful.

DETAILED DESCRIPTION OF THE INVENTION

Figure 1:
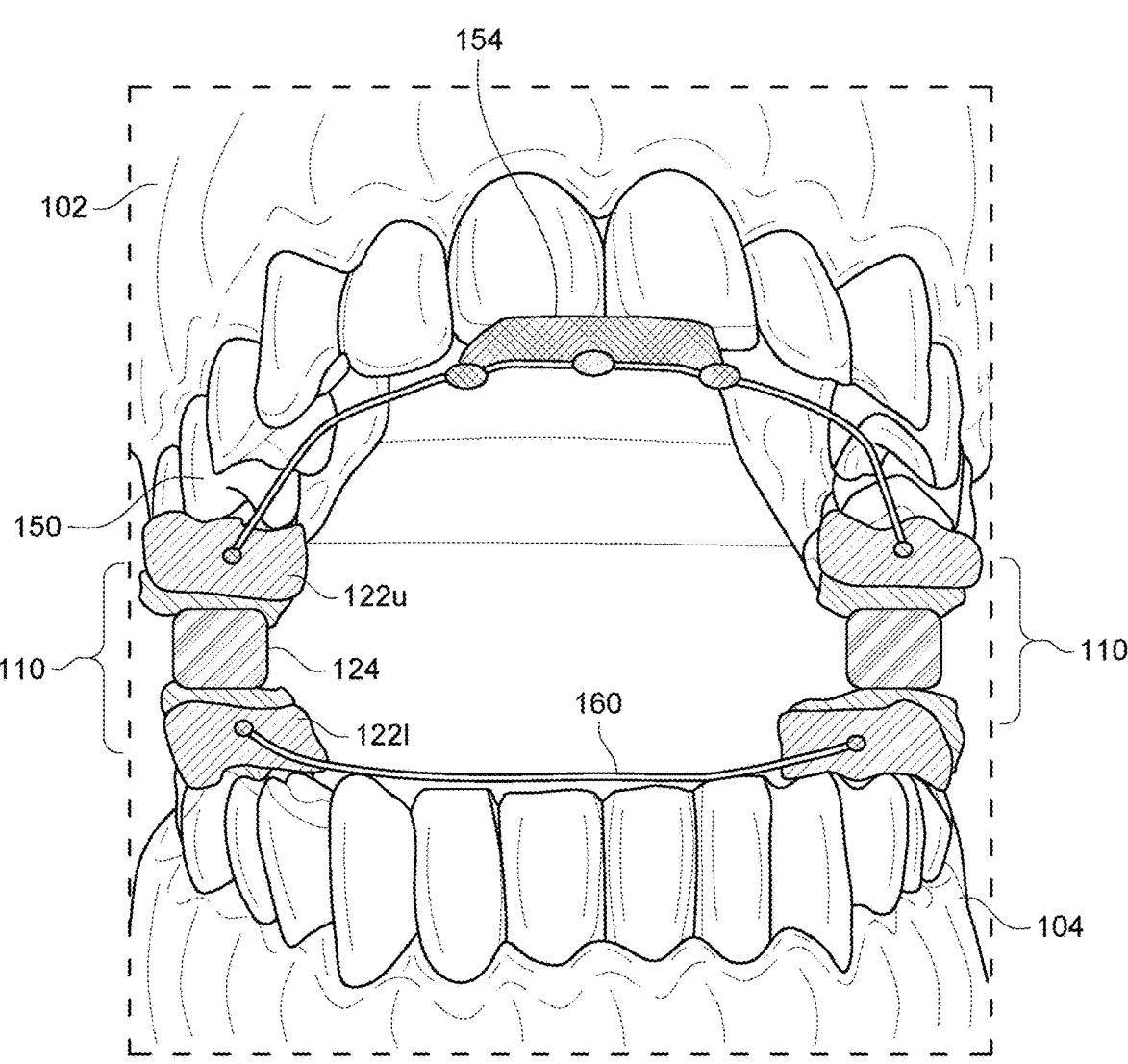
FIG. 1 shows an overview of how the mouthpiece device fits between a human user's upper and lower jaws.

FIG. 1 shows an overview of how the mouthpiece device (see FIG. 2 100) fits between the upper (102) and lower jaws (104) of a human user. This device typically comprises at least two pivoting dental blocks (110) that fit on opposite sides of the user's jaw. These pivoting dental blocks are connected to each other by an upper (150) and lower (160) archwire. Each pivoting dental block has an upper and lower wire interface face (122u, 122l), and is configured to accept an archwire end (151). The upper archwire (150) also has a lip-opening fixture (154). Here the pivots (124) are spring pivots configured to both pivot and apply an opening force to the dental block.

In some embodiments, the device may further comprise a rechargeable battery. For low power draw situations, such as powering a processor, one or more sensors, and an optional low energy wireless transceiver such as Bluetooth Low Energy (BLR) transceiver, this rechargeable battery may be positioned inside one or more of the pivoting dental blocks (110). However, for higher power use situations, such as when the device may have one or more torque applying electronic actuators, then a larger rechargeable battery may be used, which may fit outside of the pivoting dental blocks. This option will be discussed in more detail in FIG. 15 and FIG. 16 shortly.

Put alternatively, in some embodiments, the invention may be a method of using an adjustable mouthpiece device (100) to facilitate the breathing of a human user during sleep, as well as the device (100) itself. The method typically comprises adjusting this adjustable mouthpiece device (100) to fit at least some of the mouth, jaw, teeth, and lips of this human user. The adjustable mouthpiece device (100) itself is relatively complex, and can comprise various components described below.

The device typically comprises at least two pivoting dental blocks (110). Each of these pivoting dental blocks are configured to fit inside opposite sides of the user's jaws (102, 104), usually in the back of the jaw over the user's rear molars. The dental blocks may often be a composite of different materials, with the overall structure formed from materials such as polyethylene-polyvinylacetate copolymer (EVA), silicone, or acrylic resin, or other lightweight, hypoallergenic materials. These may be supplemented by other materials, including metals or alternative plastics for pivots, springs, and screws, and softer deformable plastics for sections of the dental blocks that come into contact with the user's teeth.

These pivoting dental blocks (110) are connected by an upper (150) and lower (160) archwire. Each archwire comprises two wire ends (see FIG. 2, 151), and is generally curved in a "U" shaped structure, roughly following the contours of the patient's dental arch, where each archwire has about 170-190 degrees of curvature so that both wire ends fit inside of the user's mouth. Here common dental or orthodontic archwire materials, which are often made from stainless steel, nickel Titanium, and Beta Titanium may be used. The archwire material and thickness may be chosen to optimize certain spring-force aspects of the invention, as will be discussed shortly.

Each pivoting dental block (110) will typically comprise gap-separated upper (122u) and lower wire (122l) interface faces, as well as gap-separated upper and lower fastener faces (see FIG. 2, 130u), upper and lower tooth-accepting faces (see FIG. 3 132u, 132l), and at least some other faces.

Each gap-separated upper and lower wire interface faces (122u, 122l) will typically comprise a wire hole (FIG. 2, 124) configured to admit one of the archwire wire ends (151). Thus, when these wire ends (151) are inserted into the wire holes (124), and fastened (often with a screw, although adhesive may be used) to the upper and lower wire interface faces (122u, 122l), the upper archwire (150) connects the upper wire interface faces (122u) of the two pivoting dental blocks. Similarly, the lower archwire (160) connects the lower wire interface faces (122l) of the two pivoting dental blocks (110).

To apply gentle force to open the user's lips, at least the upper archwire (150) may be further configured with a lip opening fixture (154). This is usually positioned midway between the upper archwire's wire ends (151). The lip opening fixture is configured to extend outside of the user's jaw and past at least a middle portion of the user's upper lip (see FIG. 4, 170u). Usually this will only extend a fraction of an inch, such as ¼ to ½ inch past the lip, to apply an elevation force to partially elevate the user's lip (170u) enough above its normal resting state to allow air to enter and exit. Here, the lip opening fixture and archwire can be selected to be partially bendable so that the user can adjust them for optimal comfort and performance.

In a preferred embodiment, the upper and lower tooth-accepting faces (132u, 132l) further comprise recesses configured to accommodate at least some of said teeth. The tooth-accepting faces need not be made from the same material as the bulk of the pivoting dental block, but instead may be made from alternate materials. These alternate materials can include thermoplastic materials that deform upon application of heat, but then harden, so that the patient can initially customize the tooth accepting faces by heating the dental blocks, biting into the tooth accepting faces, and then allowing the dental blocks to cool, producing tooth accepting faces that are customized to the shape of the user's teeth (usually the user's back molars).

In some embodiments, the adjustment further comprises configuring the pivoting dental blocks (110) and said gaps to exert opposite torque (e.g. by any of an actuator or by spring-action) forces on said upper and lower tooth-accepting faces (132u, 132l). This is often done by selecting the configurations and materials used in various springs and spring-like components associated with the pivoting dental blocks, as will be discussed shortly.

These torque or spring-action forces are selected to be greater than the minimum amount needed to by the user to partially open their jaws (102, 104), but less than the maximum amount needed by the user to close said jaws against said spring-action forces. It is anticipated that these will differ between users, and some experimentation and adjustment will be required to customize the device for each user.

These adjustments will typically further comprise adjusting the lip opening fixture (154), so that when the user's face is in a relaxed resting state, the torque or spring-action forces acting on the lip opening fixture and the lip opening fixture (154) itself enable the user to breathe through their mouth. However, when the user activates their jaw muscles or lip muscles to close their mouth, the user's jaw muscles and lip muscles should be able to easily overcome the opening torque or spring-action forces on both the jaws and lip opening fixture. The idea is to enable the user, while asleep, to close their lips and/or swallow saliva without conscious effort. Thus, the user can generally breathe through their mouth, while at the same time avoiding a dry mouth and/or drooling.

In some embodiments, the device may be further configured with a multi-stage drool defense configuration. Front micro grooves can be used redirect saliva to throat, replaceable medical foam pads, and an optional anti reflux valve that closes during user inhalation/swallowing may also be used.

Figure 6:
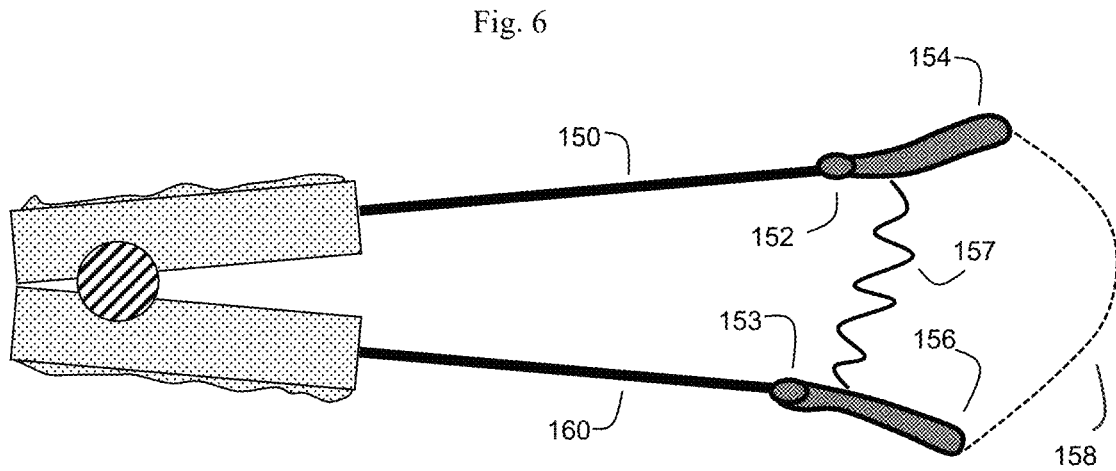
FIG. 6 shows a side view of the device, showing that in some embodiments, both the upper and lower archwires may be equipped with lip-opening fixtures, and an optional mouth covering.

In some embodiments, as discussed in FIG. 6, dry mouth may be further avoided by applying a thin flexible fabric to the end of the device to help trap moisture, as desired.

Figure 2:
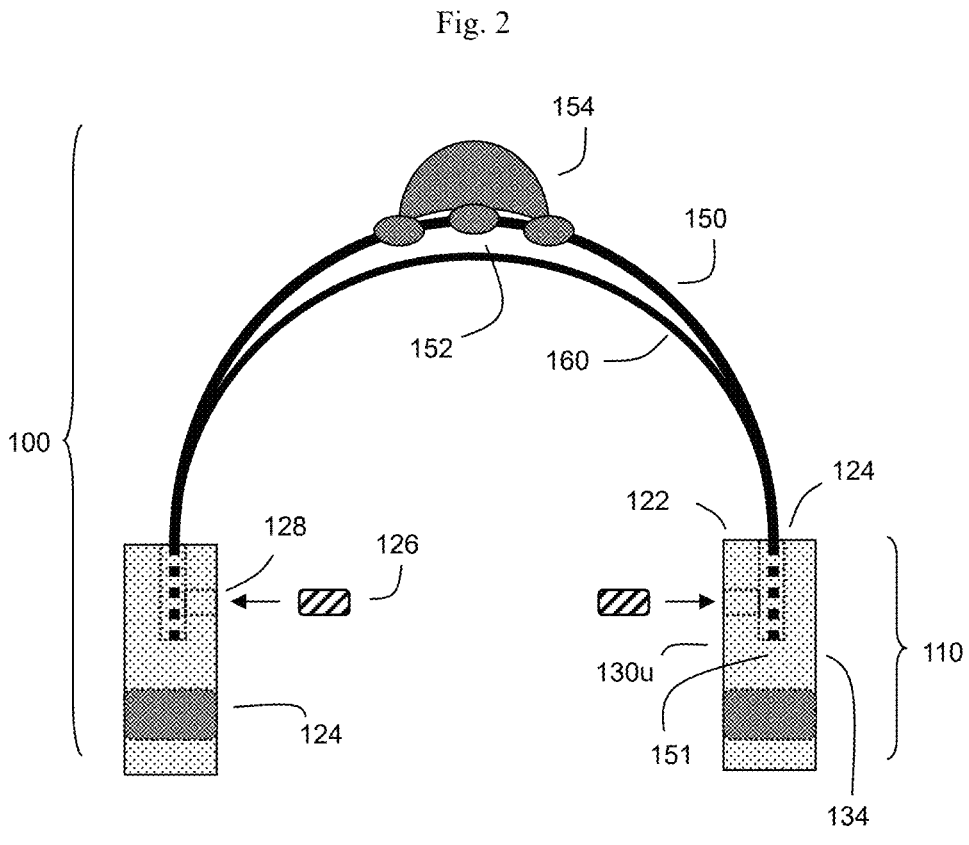
FIG. 2 shows an overhead view of the mouthpiece device.

FIG. 2 shows an overhead view of the mouthpiece device (100). This shows a top view of the dental blocks (110), as well as the upper (150) and lower (160) archwires. A lip-opening fixture (154) is attached to the upper archwire (150). The archwires fit inside wire holes (124) in the wire interface faces (here only the upper faces 122*u* are shown), and can be held in place by screws (126) inserted into screw holes (128) in the upper and lower fastener faces (130*u*, 130*l*, here only 130*u* is shown). In some embodiments, spring-action tension devices may be placed along the outside (cheek side) of the dental blocks (110), in which case these cheek-side faces are designated "tension-mount faces" (134*u*, and 134*l*). Here again, as before, (134*u*) would be the tension mount face on the upper portion of the dental block (110), while (134*l*) would be the tension mount face on the lower portion of the dental block.

Adjustments for Growing Jaws During Childhood:

Children's jaws grow during childhood, and a device initially configured to fit the dimensions of a younger child's jaw may fit less well as the child ages and the child's jaw grows. Although large changes in jaw size, or the growth of new back molars, may require that the device be refitted, smaller changes can often be accomplished by, for example, loosening screws (126), pulling the ends of the archwires closer towards the edge of the wire holes (124), and then tightening screws (126). In some embodiments, to make small changes to the shape of the arch, additional holes and screws may be placed in the dental blocks to apply side forces to the archwires, thus resulting in minor changes in archwire shape. In still other embodiments, additional fixtures may be placed near the center or archwire, such as at or near the lip-opening fixture (154), which can apply or relax tension on the archwire, thus also effecting minor alterations in the archwire's shape.

Figure 3:
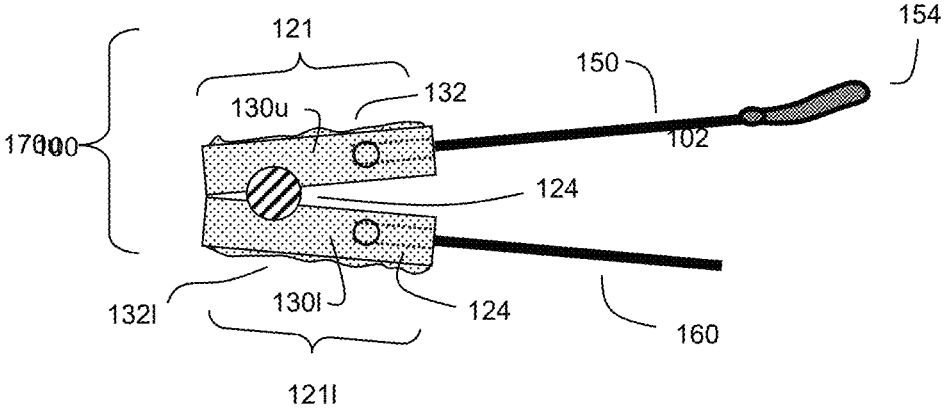
FIG. 3 shows a side view of the mouthpiece device, here seen from a bisected view from inside the user's jaw.

FIG. 3 shows a side view of the mouthpiece device (100), here seen from a bisected view as if from inside the user's jaw. This enables the upper and lower fastener faces (130*u*, 130*l*) to be more easily seen.

In this embodiment, the pivoting dental blocks (110) are each divided into an upper portion (121*u*) and a lower portion (121*l*), and the two portions are connected by a mechanical pivot (124). The upper portion has a tooth-accepting face (132*u*) that has recesses that can accommodate the user's upper molars or other teeth. The lower portion also has a tooth-accepting face (132*l*) with recesses that can accommodate the user's lower molars or other teeth.

A lip-opening fixture (154) is attached to the upper archwire (150), but (in this example) not to the lower archwire (160). The dotted lines show the approximate locations of the wire holes (124) inside the dental blocks.

Put alternatively, in some embodiments, the pivoting dental blocks (110) comprise an upper portion (121*u*) and a lower portion (121*l*). In this embodiment, these portions are connected by a mechanical pivot (124). The upper wire interface face (122*u*), upper fastener face (130*u*), and the upper tooth accepting face (132*u*) are positioned on said upper portion (121*u*). By contrast, the lower wire interface face (121*l*), lower fastener face (130*l*), and lower tooth accepting face (132*l*) are positioned on the lower portion (121*l*).

In some embodiments, the mechanical pivot can comprise a spring, which serves both as a pivot and to provide at least some of the jaw-opening spring forces. In other embodiments, the mechanical pivot (124) can comprise a ball joint or a torque applying electronic actuator. Here the jaw opening spring forces may be provided by alternative types of spring devices, or by electromagnetic actuators, to be discussed shortly.

In some embodiments, when at least one torque applying electronic actuator is used, this at least one torque applying electronic actuator may be configured to exert opposite torque forces on the pivoting dental blocks, such as at the upper and lower tooth-accepting faces.

Figure 4:
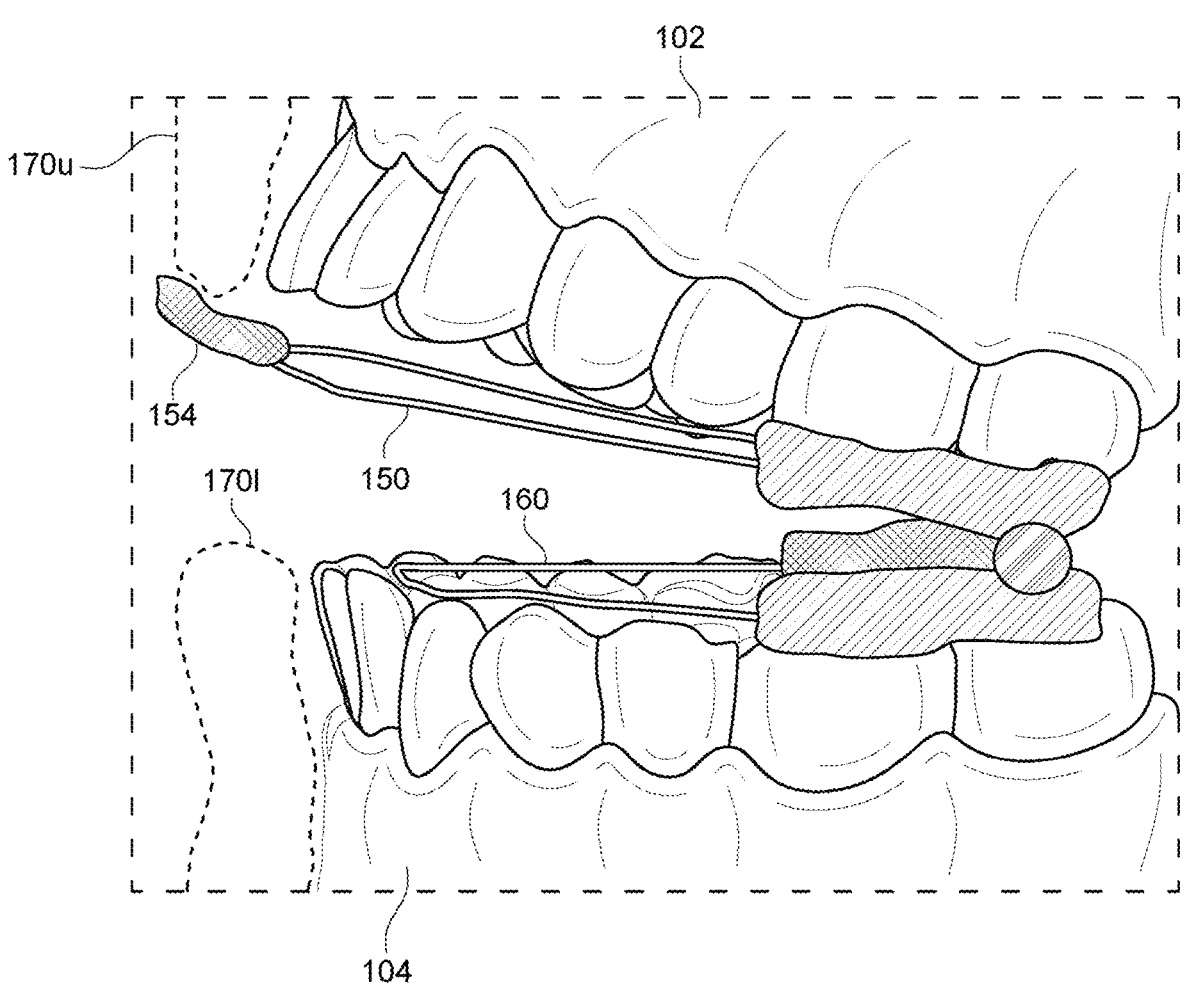
FIG. 4 shows a side view of how the mouthpiece device can fit between the upper and lower jaws of a human user and apply a gentle force to open both the user's jaws and the user's lips.

FIG. 4 shows a side view of how the mouthpiece device (100) can fit between the upper (102) and lower (104) jaws of a human user and apply a gentle force to open both the user's jaws and the user's lips (170*u*, 170*l*). Here the approximate outline of the human user's upper and lower lips (170*u*, 170*l*) is shown in dashed lines. As previously discussed, the lip-opener fixture (154) is configured so that when the device is inserted in the user's mouth, the lip-opener fixture can protrude slightly (usually ¼ inch to ½ inch) between the user's lips (170*u*, 170*l*) and apply a gentle opening pressure to at least the user's upper lip (170*u*) when the user's lips are relaxed.

In this disclosure, "gentle force" means enough force to open the jaws or lips when the jaw or lip muscles are relaxed but not enough force to open the jaw or lips when the jaw or lip muscles are working to close the jaws or lips.

To support the lip opening fixture, in some embodiments, at least the upper archwire (150) may further comprise at least one upper attachment device (152) disposed midway between the opposite sides or ends (151) of the archwire. The lip opening fixture (154) often comprises at least one upper lip opening fixture configured to attach to this at least one upper attachment device (152). However other embodiments are possible.

Figure 5:
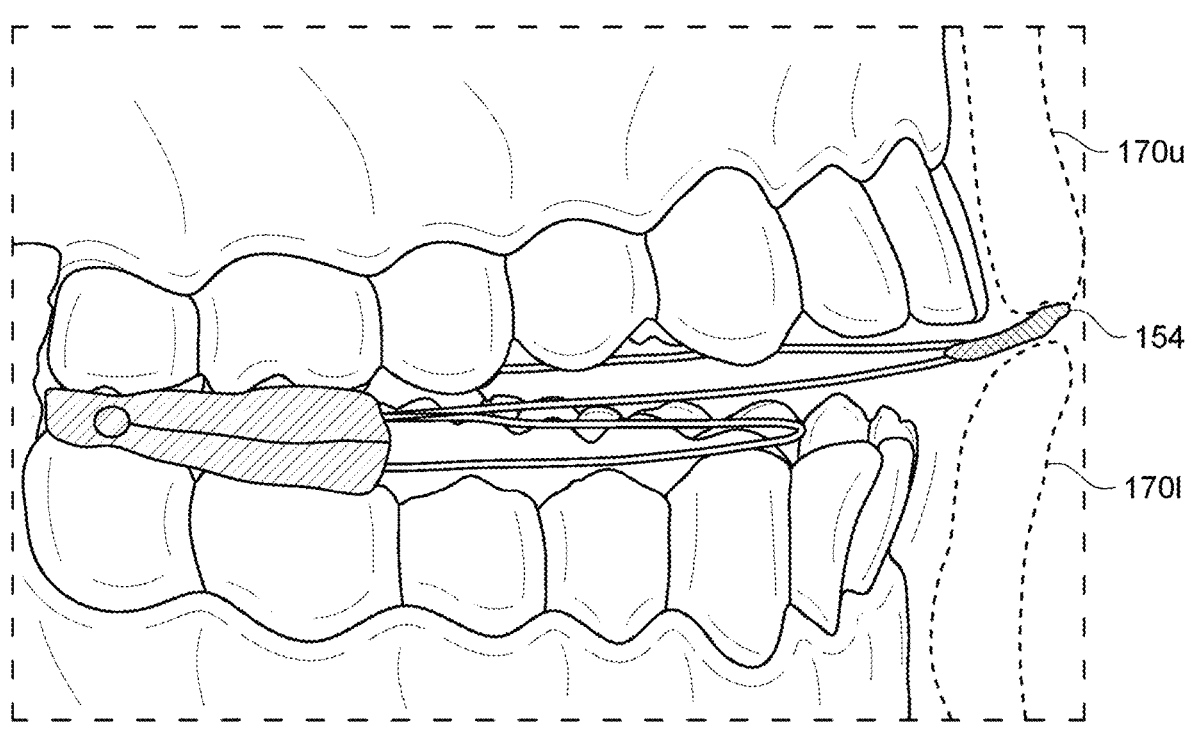
FIG. 5 shows a side view of how the device's mouth opening force can also be selected to enable the human user to easily close their jaws to swallow when desired.

FIG. 5 shows a side view of how the device's mouth opening force can also be selected to enable the human user to easily close their jaws to swallow when desired. Similarly, the lip opening fixture (154) can be configured so that the human user can also easily close their lips to swallow. The jaw opening force can be adjusted by selecting suitable springs on the pivoting dental blocks. This lip opening force adjustment can be done by selecting the stiffness and spring action of the archwires (150) and the lip-opener fixture (154).

FIG. 6 shows a side view of the device, showing that in alternative embodiments, both the upper (150) and lower archwires (160) may be equipped with lip-opening fixtures (154, 156).

Note that the lower archwire (160) itself can comprise a lower attachment device (153) disposed midway between the archwire's opposite sides or ends (151). In this embodiment, the lip opening fixture comprises at least one lower lip opening fixture (156) configured to attach to at least one lower attachment device (153).

In embodiments, when there are two lip opening fixtures, the upper lip opening fixture and the lower lip opening fixture may further comprise (and be connected by) a lip opening spring (157) configured to separate the user's lips while these lips are relaxed.

In some embodiments, the device may further comprise an attached covering (158) that can, for example comprise any of a woven or nonwoven fabric, fiber, hydrogel, or humidity absorbent polymer. This covering is intended to extend outside the user's mouth, and to allow air to enter and exit the user's mouth, while, at the same time, trapping at least some moisture (often from the user's breath or mouth) to help prevent the user's mouth from becoming overly dry.

Other Mouth Humidification Systems and Methods

In some embodiments, the optional humidification system may be an integrated device that can be further disassembled into multiple functional parts to adapt to different application scenarios.

For example, in some embodiments, the mouthpiece device may be designed to interface with an optional continuous positive airway pressure (CPAP) device or other mechanized front-end device, creating a more complex humidification front end for the mouthpiece device. In this embodiment, the optional humidification structure may be divided as follows.

1. Main humidification shell: The main humidification shell may accommodate the power structure as a whole, independent modules can be installed at the ventilation port of the respiratory assist device.

2. Filtering part (back): A filtering part may also be installed near the front of the mouthpiece device, creating an optional air inlet. This optional air inlet may be used to filter foreign objects, hair, and dust, and can use replaceable materials such as electrostatic cotton and HEPA filters.

3. Humidification section (central core): This can either be a passive humidification structure: filled with ultra-fine fiber, hydrogel or super absorbent polymer, providing humidity through natural evaporation of air. This is a simple structure, and does not need its own power supply. Alternatively, the humidification section may be an active humidification structure. This may include various active humidification elements, such as an ultrasonic atomization sheet or micro heating device configured to actively produce fine mist. Such active humidification elements will typically require electrical power, and may also employ an intelligent control system. This can include a humidity sensor module, capable of detecting intake humidity and intelligently determining whether to activate active humidification. Thus, for example, when the environmental humidity reaches a certain threshold (such as 50% or above), the intelligent control system can automatically shut down to save energy;

4. Optional rotating auxiliary unit: In some embodiments, when hydrogel humidification elements are being used, either the air flow itself, and/or optional hydrogel rotation motors may be employed to drive the hydrogel to rotate. This exposes the hydrogel to the ambient humidity more uniformly, which can improve the humidification efficiency and extend the moisture release cycle.

Figure 7:
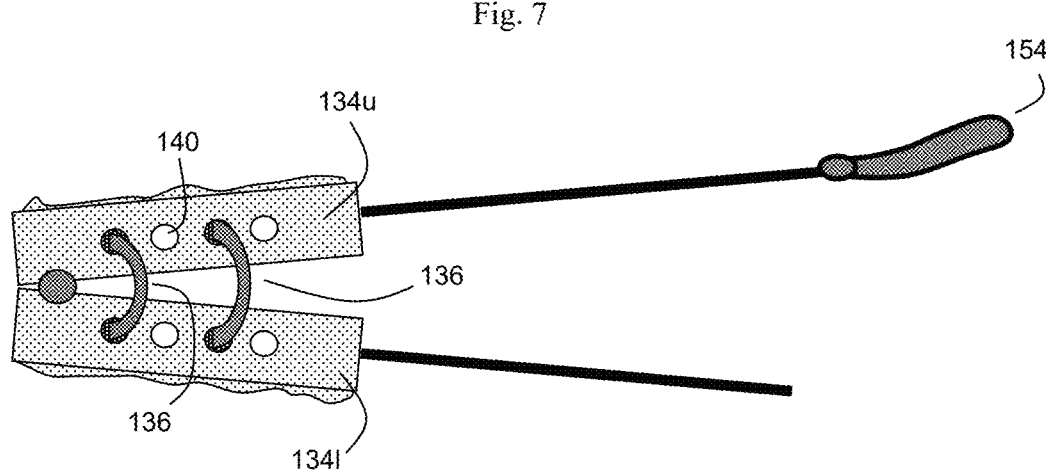
FIG. 7 shows an alternate side view of the device, showing how at least one deformable spring-like material can be mounted on various positions along a series of tension mount holes.

FIG. 7 shows an alternate side view of the device, showing how at least one deformable spring-like material (here, two materials 136a and 136b are shown) can be mounted on various positions along a series of tension mount holes (140) positioned on the device's upper and lower tension mount faces (134u, 134l). This also allows the spring-action forces to be adjusted for a given user. These materials can, for example, be elastic materials selected with a tendency to transition from a curved shape to a more linear shape with the desired amount of force.

Figure 8:
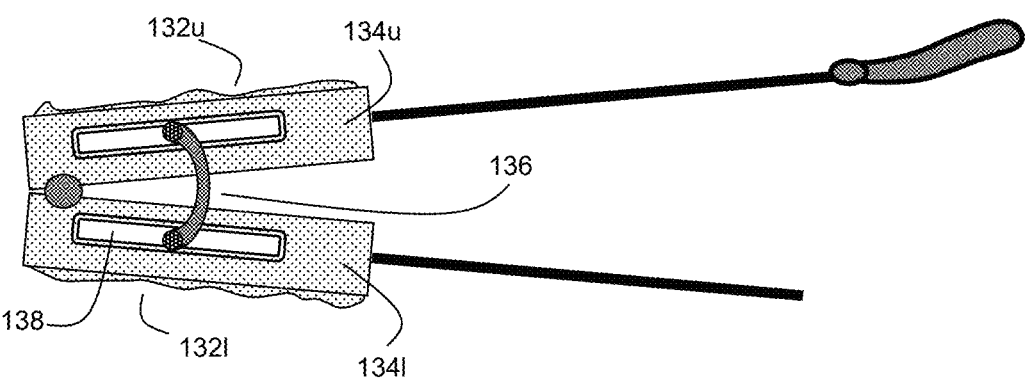
FIG. 8 shows an alternate side view of the device, showing how at least one deformable spring-like material can be mounted on various positions along a slot on the device's upper and lower tension mount faces.

FIG. 8 shows an alternate side view of the device, showing how at least one deformable spring-like material (136a) can be mounted on various positions along a slot (138) on the device's upper and lower tension mount faces (134u, 134l). This also allows the spring-action forces to be adjusted for a given user.

In some embodiments, the pivoting dental blocks (110) may further comprise gap-separated upper and lower tension mount faces (134u, 134l). These upper and lower tension mount faces are typically disposed both parallel to the gap-separated upper and lower fastener faces (130u, 130l) and also perpendicular to the upper and lower tooth-accepting faces (132u, 132l).

These upper and lower tension mount faces (134u, 134l) are termed this because they are the faces where various optional spring like materials may be mounted. Often this face is chosen as to avoid irritating the user's tongue, which will be on the opposite side of the dental block.

These upper and lower tension mount faces will typically further comprise any of a slot (138) or a plurality of mounting holes (140). This slot or plurality of mounting holes is configured to accept at least one deformable spring-like material (136a, 136b). This spring-like material is selected or configured so that, when disposed between the slots or mounting holes (and often affixed by screws), it exerts the appropriate amount of spring-force directed to cause the gap to widen (often against the opposing force of the user's jaw when the jaw muscles are relaxed). Examples of suitable spring-like materials include deformable nickel-aluminum (nitinol) wires, elastomers, synthetic rubber, silicone, and the like.

Remember that there are two dental bocks (110). Thus often, the at least one deformable spring-like material comprises two deformable spring-like materials, one for each block, so that each material is connected to one of the pivoting dental blocks.

In some embodiments, however, employing more than one deformable spring-like material per dental block may be useful. Thus, in these embodiments, the at least one deformable spring-like material may comprise more than two deformable spring-like materials. Here at least one of the pivoting dental blocks is connected to more than one of these deformable spring-like materials.

Alternative Configurations

Figure 9:
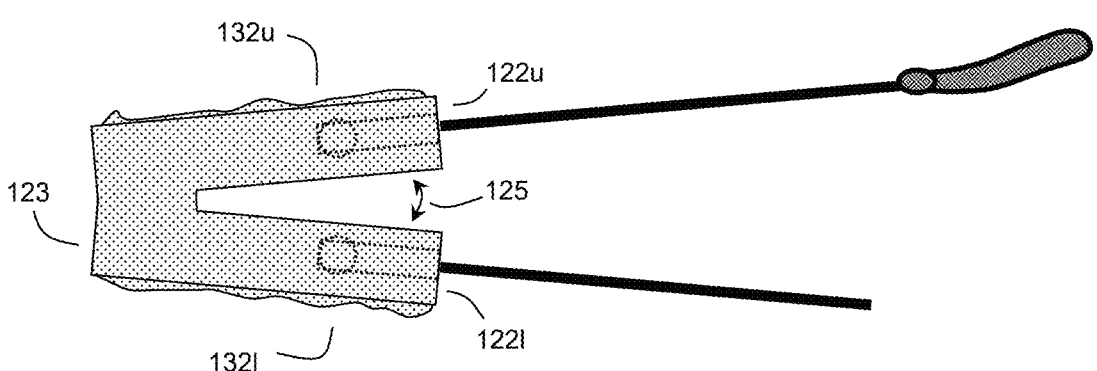
FIG. 9 shows that in some embodiments, the pivoting dental blocks can comprise a single portion of material partially bisected by a gap that divides the block into an upper portion and a lower portion on the wire-facing faces, with a single portion on the opposite face or side.

In some embodiments, the main portion of the dental block may be comprised of a material selected for elasticity to generate adequate spring-like forces. Such elastic materials can comprise Nylon (e.g. a $(C_{12}H_{22}N_2O_2)$ n polymer, such as a hexanedioic acid, 1,6-diaminohexane polymer often referred to as Nylon-6,6). FIG. 9 shows that in some embodiments, the pivoting dental blocks (110) can comprise a single portion of a block material partially bisected by a gap (125) that divides the block into an upper portion and a lower portion on the wire-facing faces (sides 122u, 122l), with a single portion on the opposite face or side (123).

In these embodiments, the pivoting dental blocks (110) can comprise a single portion of block material partially bisected by a gap (125) that divides the dental block into an upper portion (122*u*) and a lower portion (122*l*) on the front wire-facing side, but only a single portion (123) on an opposite side. In this embodiment, the upper wire interface face (122*u*), upper fastener face (130*u*), and upper tooth accepting face (132*u*) are positioned on the upper portion. By contrast, the lower wire interface face (122*l*), lower fastener face (130*l*), and lower tooth accepting face (132*l*) are positioned on the lower portion. In this embodiment, the pivoting dental blocks comprise an elastic material selected to be capable of repeatedly pivoting about said single portion (123).

Other Lip-Elevating Fixture Embodiments

Figure 10:
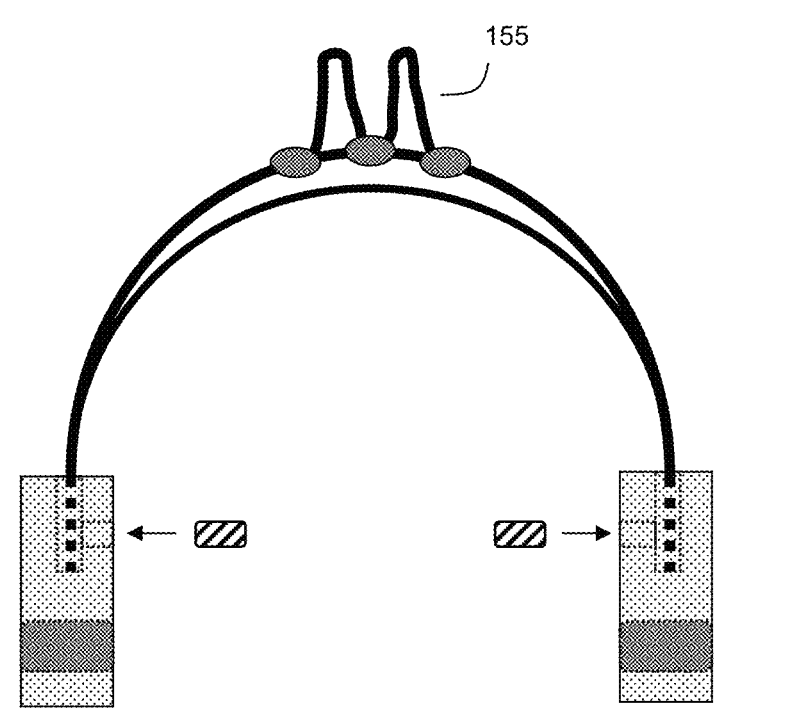
FIG. 10 shows that in some embodiments, the lip-elevating fixture can comprise at least one archwire fold configured to protrude between the middle of the user's lips.

FIG. 10 shows that in some embodiments, the lip-elevating fixture (154) can comprise at least one archwire fold (155) configured to protrude between the middle of the user's lips.

In this embodiment, the lip opening fixture comprises at least one archwire fold. This archwire fold is configured to protrude out of the middle of the user's mouth, and may also be further bent at an upward angle to elevate at least the middle of the lips when the lips are in a resting configuration.

Although for simplicity, only a single archwire has been shown for the upper and lower archwires (150, 160), this need not be limiting. In some configurations, to achieve the proper combination of strength and flexibility/rigidity, any of the upper and lower archwires may comprise a plurality of archwires.

About Adjusting the Device

As previously discussed, human users will vary in both jaw and mouth dimensions, as well as in jaw and lip muscle muscular strength and flexibility.

In terms of adjusting the size and shape of the device, in some embodiments, each of the gap-separated upper (130*u*) and lower (130*l*) fastener faces can comprise screw holes (128). These are aligned perpendicular to the wire holes (124) and in contact with these wire holes. These screw holes are configured so that a screw (126) inserted into the screw hole can be used to fasten the archwire wire ends (151) to the pivoting dental blocks (110). This allows for some adjustment.

For example, this adjustment can further comprise altering any of a length of said upper (150) or lower (160) archwire, or altering the distance of which any of said upper or lower archwire wire ends (151) enter any of the wire holes (124). Further, as previously described, the upper (132*u*) and lower (132*l*) tooth accepting faces can be adjusted (e.g., using thermoplastic material, and instructing the patient to bite into the thermoplastic material when it is hot) so that the adjustable mouthpiece device fits comfortably into the user's mouth.

Adjusting the Spring Forces:

Often, spring forces may be adjusted by providing a series of different spring pivots or spring-like materials and selecting those best suited to a given user. As a general guideline, the previously discussed work of Takai and Brunton suggest that the spring pivots or spring-like materials should be selected to provide a minimum amount of force greater than 4 Newtons of force and a maximum amount of force of less than 25 Newtons of force.

Figure 11:
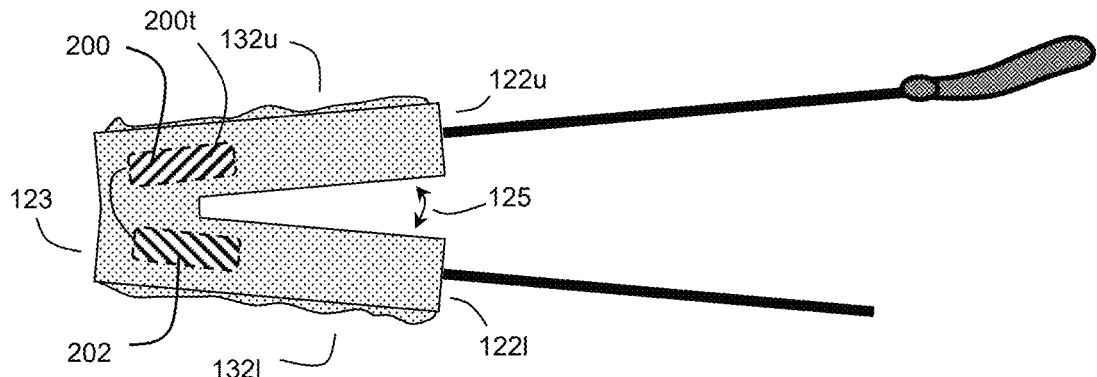
FIG. 11 shows that in some embodiments, the pivoting dental blocks (or other portions of the device) may also comprise an embedded computer processor (e.g., a microprocessor), sensor, and optional transceiver such as a Bluetooth™ transceiver.

Automatically Adjusting the Spring Forces as a Function of the User's Physiological State:

FIG. 11 shows that in some embodiments, the pivoting dental blocks (or other portions of the device) may also comprise an embedded computer processor (e.g., a microprocessor, 200), an embedded sensor (202), and optional embedded wireless transceiver such as a Bluetooth™ transceiver (200*t*). In some embodiments, the embedded processor (200) may comprise an embedded wireless transceiver (200*t*) so that the two units are on the same chip and packaged together.

Here, this arrangement (at least one embedded processor 200 and at least one embedded sensor (202) may be used to automatically monitor at least one physiological status of the human user during sleep. This data can either be stored in the processor's memory and/or be transmitted using an optional embedded wireless transceiver (200*t*) to an external computerized device, as will be discussed shortly in FIG. 13.

In this embodiment, at least one processor comprises at least one embedded mouthpiece processor (200), often configured with an embedded wireless transceiver (200*t*). The embedded devices may be stored in various locations in the mouthpiece device, but it is often convenient to place them in at least one of the upper and lower portions of at least one of said pivoting dental blocks (FIG. 1, 110), as shown in FIG. 11.

In some embodiments, at least one of the various sensors (202) is at least one embedded mouthpiece sensor. Various sensors, such as pulse oximeters, temperature and moisture, air flow, and other types of sensors, can be used here. In a preferred embodiment, the embedded mouthpiece sensor(s) are configured to transmit data to at least one embedded processor (200) and wireless transmitter (200*t*). This data can then be wirelessly transmitted to various types of external computerized devices.

In some embodiments, these sensors can also detect any of humidity and airflow as well. The data from these sensors can be transmitted to external computerized devices, and used for various applications such as analyzing sleep patterns and sleep quality, analyzing sleeping cycles and breathing patterns (mouth breathing vs. nose breathing), detect possible health issues that could occur when sleeping and warn the user, hypoventilation (shortness/shallow breathing), detect mouth dryness while sleeping, make health suggestions (sleep times, amount, proper hydration), connect to smart devices like thermostat, humidifier, and automatically adjust these various smart devices to adapt for comfortable sleeping without manual adjustment In some embodiments, the system can use a suitable smartphone app, or other software to transmit the information to a smartphone user interface. This can be used to view collected data about sleep patterns and behavior, modify app settings, connect to devices and smart devices via Bluetooth, and enable/disable various device features.

Circuit parts for these embodiments can include a microcontroller w/a BLE (low-energy Bluetooth transceiver for smart device connection). Additional parts can include the previously discussed humidity sensor and airflow sensors. These electrical components can exchange data with the microcontroller with an inter-integrated circuit communications protocol such as I2C or other method. This will often be powered with a rechargeable battery (as discussed elsewhere), regulated with low dropout (LDO) regulators as needed.

Example Connection:

In some embodiments, the adjustable mouthpiece device further comprises at least one processor-controlled actuator. Here, at least one processor (such as embedded processor 200) is configured to control these various processor-controlled actuator(s). This enables the processor-controlled actuator(s) to adjust the minimum and/or maximum opening force. This can be done, for example, by directing the actuator(s) to increase the minimum opening force by less than 1 Newton of force or decrease the minimum opening force by less than 1 Newton of force.

Figure 12:
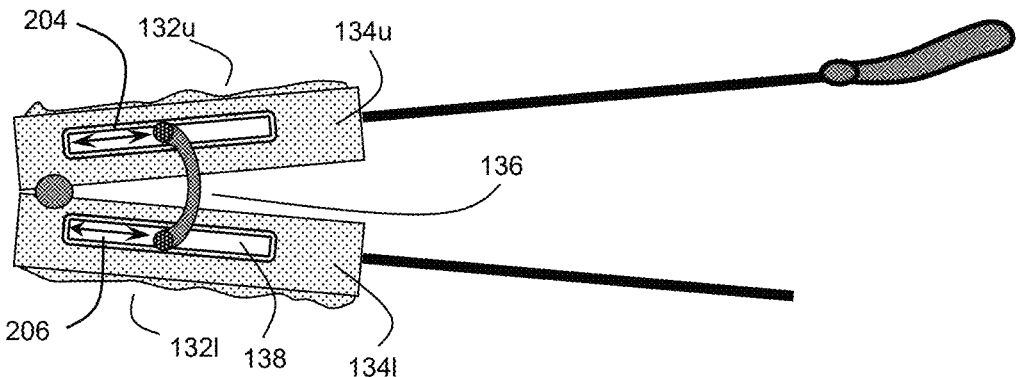
FIG. 12 shows that in some embodiments, the pivoting dental blocks (or other portions of the device) may also comprise at least one processor-controlled actuator configured to adjust the device's mouth opening force upon commands from the processor.

FIG. 12 shows that in some embodiments, the pivoting dental blocks (or other portions of the device) may also comprise at least one processor-controlled actuator (204, 206) configured to adjust the device's mouth opening force upon commands from the processor. In the embodiment shown in FIG. 12, two actuators (204) and (206) are being used to control the position of the deformable spring-like material (136) in slots (138), similar to the arrangement previously discussed in FIG. 8. Here, one side of the pivoting dental blocks is shown. The other side has a similar arrangement. Thus, four actuators would be used for both sides of the mouth.

Figure 13:
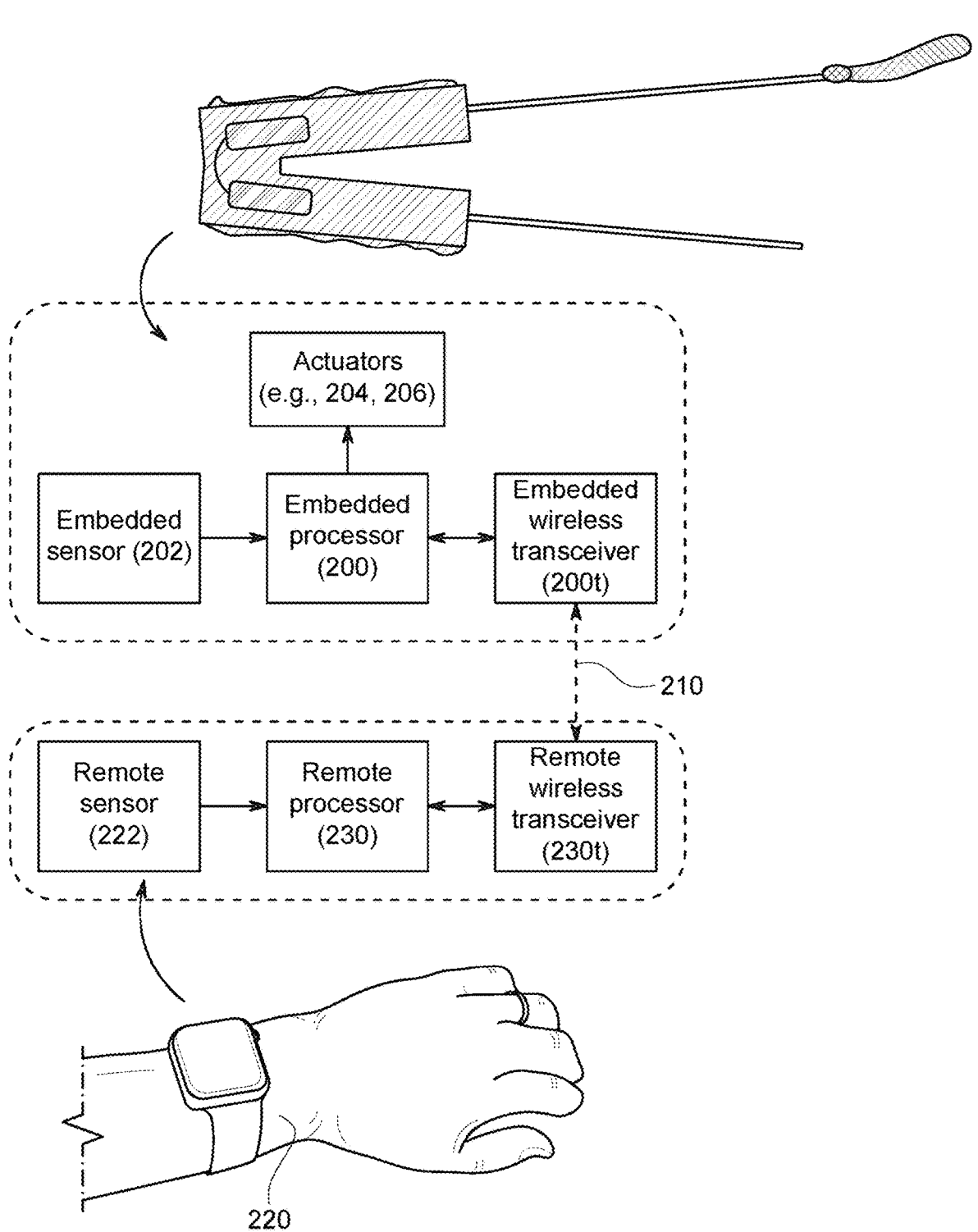
FIG. 13 shows that in some embodiments, the mouthpiece device may be configured to wirelessly send and receive data (e.g., send embedded sensor data, receive actuator commands) to and from a nearby computerized device, such as a smartwatch or other nearby computerized device.

FIG. 13 shows that in some embodiments, the mouthpiece device may be configured to wirelessly send and receive data (e.g., send embedded sensor data, receive actuator commands 210) to and from a nearby computerized device, such as a smartwatch (220) or other nearby computerized device (e.g. smartphone, tablet computer, etc.). Examples of such devices include the popular Apple Computer iOS based iWatch and iPhone, as well as the popular Android based watch and smartphone products.

In this embodiment, the at least one processor comprises an external or remote processor (230). This external processor is configured to receive data from at least one sensor. Here the method uses this external processor and this data to adjust a processor-controlled actuator (such as 204, 206) to adjust any of the minimum amount and the maximal amount of opening force. Here, for example, the external processor (230) can use its transceiver (230t) to wirelessly transmit commands (210) to the embedded wireless transceiver (200t) and the embedded processor (200). The embedded processor (200) can then control the actuators (204, 206) as previously discussed As shown in FIG. 13, in some embodiments, the external processor (230) is in the form of an external wrist-mounted computerized device (220). This external computerized device (220) can also comprise an external wireless transceiver (230t). Here, the external processor (230) can be configured to receive data from either an embedded mouthpiece sensor (202) and/or a wrist-mounted computerized device sensor (222). Here, the external/remote processor (230), along with its external wireless transceiver (230t), can use this sensor data to adjust the processor-controlled actuator (204, 206) according to this data.

Actuator Types

Figure 14:
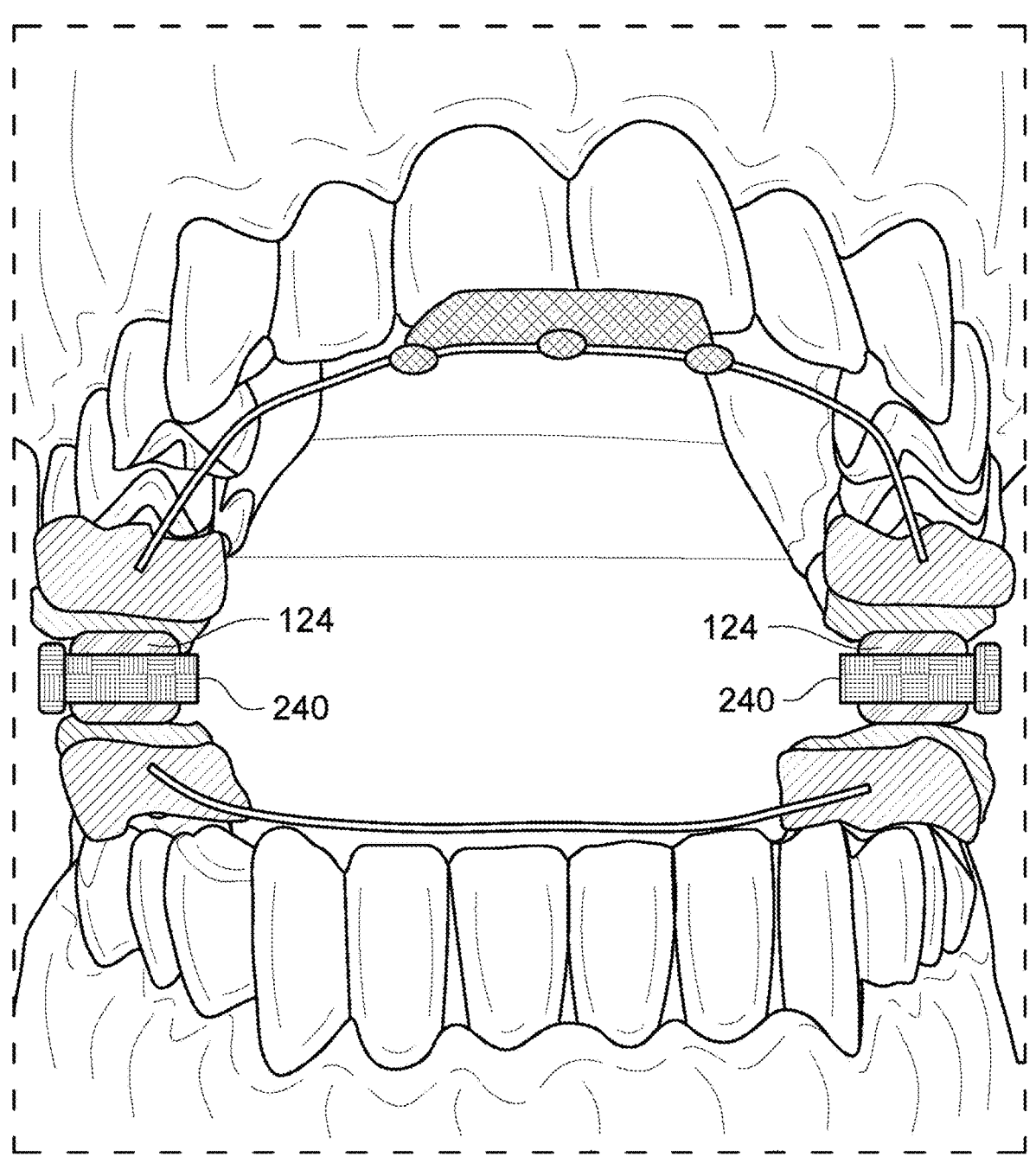
FIG. 14 shows an alternate location where the actuators may be placed.

Various types of actuators may be used in this device. These include:

1: Pneumatic actuators that operate by processor-controlled thermal expansion/contraction of air stored in small airbags. Here small silicon air pockets (240) are placed at the pivot regions (124), as shown in FIG. 14. The volume of the air in the air pockets can be regulated by using processor-controlled heating or cooling elements that heat up or cool the air, thus changing the volume of the air pockets, and creating greater or less opening force as desired. This can be controlled by the embedded processor (200), or by an external/remote processor (220) and wirelessly transmitted commands (210).

2: Actuators that expand or contract in response to processor commands. These include piezoelectric materials, electro-shapeable materials, and the like. As previously discussed, such actuators may be placed in various locations, such as FIG. 12 (204, 206). Alternatively, materials that change shape or size with temperature, along with processor-controlled heating elements, may be used.

3: Electromagnetic motors and other types of electromagnetic actuators. Processor-controlled electromagnetic actuators may also be used, optionally in conjunction with various gearing arrangements.

4: Magnet-based actuators. In some embodiments, the mouthpiece may further comprise at least two magnets, which may be placed in various locations about the mouthpiece, such as at or near the lip opening fixtures (FIG. 6 154, 156). At least one of these magnets is configured to operate under the control of the embedded processor (200) so that the opening force, which is controlled by the repulsion between the magnets, can be controlled as previously discussed.

Sensor Types

As previously discussed, the system may use embedded sensors (202) and/or remote (e.g., not embedded sensors 222) to help determine the optimum opening force.

The embedded sensors (202) can include any of moisture sensors, pulse oximeters or other type of blood oxygen sensor. Additionally, other types of sensors, such as motion sensors, may be used to sense unusual amounts of mouth or body motion during sleeping, which might be indicative of user stress.

The remote/not-embedded sensors (222) can include any of pulse sensors, pulse oximeters, motion detectors, and sound sensors (to detect snoring or breathing problems). Motion sensors may also be used to sense user body motion during sleep.

Algorithm Types

In general, the system will be configured to operate according to a closed-loop feedback process. If the opening force is too low, then the user's mouth will tend to be shut more than optimal. This will tend to lead to higher levels of mouth moisture, but potentially higher levels of sleep apnea, lower oxygen levels, and potentially higher noise levels due to snoring or gasping during sleep. This can cause distress leading to higher pulse levels.

If the opening force is too high, then the user's mouth will tend to be open more than optimal. This will tend to lead to lower levels of mouth moisture, but potentially higher oxygen levels. Noise levels may also tend to be higher.

In general, the system algorithms will be designed to seek an opening force setting where the user is exhibiting lower physiological stress levels, and/or alternatively according to preset user preferences.

For example, a user who is unusually sensitive to dry mouth may inform the system that a lower opening force is desired. Alternatively, a user who exhibits lower blood oxygen levels or other evidence of respiratory distress may inform the system that a higher opening force is desired. Within these user-set parameters, any of the processors (200 or 230) may be configured to record which opening forces are associated with less evidence of user sleeping distress (such as lower motion, lower noise, normal pulse, and adequate oxygenation. The system can then use either manufacturer supplied standard parameters, or alternatively may first calibrate on an individual user during a calibration period, and then use these user-calibrated values going forward.

Rechargeable Battery Embodiments

As previously discussed, in some lower power use cases, such as when there are no electronic actuators, and the only powered elements of the device are low powered processors, sensors, and low power wireless transceivers such as Bluetooth Low Energy transceivers, any rechargeable batteries may be built directly into the pivoting dental blocks (110). However, in higher power use situations, such as when electronic actuators may be present, larger batteries with more storage capacity may be desired.

Figure 15:
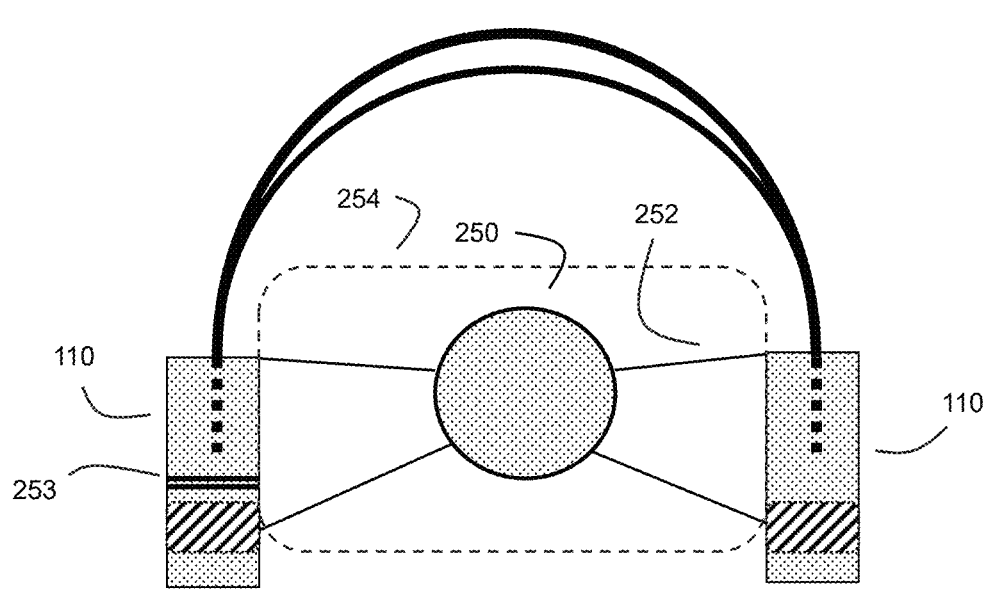
FIG. 15 shows an embodiment where a larger capacity rechargeable battery, such as a combination rechargeable battery and induction coil, may be positioned in between the pivoting dental blocks.

FIG. 15 shows an embodiment where a larger capacity rechargeable battery, such as a combination rechargeable battery and induction coil (250), may be positioned in between the pivoting dental blocks (110). Here in the embodiment shown, the combination rechargeable battery and induction coil (250) is shown suspended between the two pivoting dental blocks (110) by any of wires (252) or an optional plastic support (dashed lines 254). These wires or plastic support function to both hold the battery in place, as well as help direct power from the battery to processors, actuators, sensors, and wireless transmitters which may be located in the dental blocks (110) or in the optional plastic support (254) itself.

In some embodiments, the device may be designed to fit easily between the user's jaws and may have an optional gel mold for the back molars, as well as an optional lining of ethylene-vinyl acetate or other material around the rest of the device to fit the device for each user.

In some embodiments, the device may utilize two small 5-Newton motors/actuators mounted vertically near the front of the mouth to raise the mouth and lips around 20 millimeters while the mouth and jaw muscles are relaxed. Here, the device may raise the mouth by being attached to the ethylene-vinyl acetate or other material, supporting the mouth, raising the material, and raising the mouth.

In some embodiments, the 5-newton motors may be encased in a layer of medical-grade silicone, along with the wires, to ensure safety and the prevention of injury. The device may also be configured to periodically deactivate the motors' force, such as for about 10 seconds for every minute, to allow the user to close the mouth and swallow subconsciously.

In the case of teeth grinding or other activities that could damage the device, the ethylene-vinyl acetate liner, or other material, can be configured to absorb the damage from the teeth and mouth movement.

As previously discussed, in some embodiments, the device may be powered by a small battery (See FIG. 15, 250), which may be a circular lithium-ion battery that is completely sealed and attached to the frame of the device at the roof of the mouth. As previously discussed, in a preferred embodiment, the battery is rechargeable, which can be recharged by either snapping it into its charging port, which is connected to a power supply, by induction charging, or other methods. Additional configurations are also possible. These include modifications to the time between deactivation periods, sensors, processors, and a wireless connection to external controls.

In some embodiments, one or more of the pivoting dental blocks may further comprise at least two external electrodes, such as shown in FIG. 15 (253). These electrodes may in turn be connected to suitable charging circuitry so that the battery (250) may be charged by direct electrical contact with an outside power source This direct electrical contact can be used for fast charging (such as within 10 minutes). In some embodiments, these electrodes (253) may be made of biocompatible, electrically conducting metal, such as a titanium alloy. To facilitate connection to an external power source, these electrodes (253) may optionally be at least partially coated with a hydrophobic coating to enable the electrodes to be self-drying.

Put alternatively, at least one of the pivoting dental blocks (110) may further comprise at least two external electrodes configured to charge the rechargeable battery 250) by direct contact to an external power source. See FIG. 16 (255).

Figure 16:
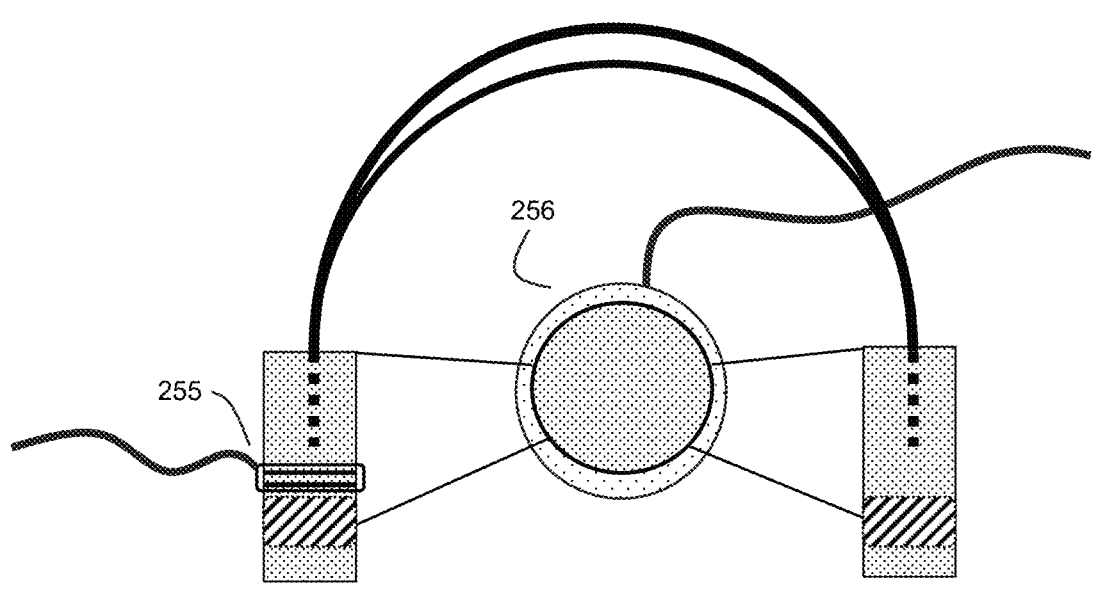
FIG. 16 shows the embodiment of FIG. 15, where the mouthpiece device may be removed from the user's mouth and charged using a magnetic induction charger.

FIG. 16 shows the rechargeable battery embodiment of FIG. 15, where the mouthpiece device may be removed from the user's mouth and charged using a magnetic induction charger (256). Here the magnetic induction charger (256) may be placed in contact with an induction coil that is also part of the rechargeable battery unit (250). The magnetic induction charger is then plugged into a voltage source (such as a 5V 20-100 milliamp charger), and the mouthpiece unit then charged during the day when the user is presumably not using the mouthpiece device.

Magnetic Charging and Direct Charging

Direct charging option: Various methods may be used to charge the unit. In some embodiments, it may be useful to configure the unit for direct fast charging (e.g. 10-minute charging) by embedding electrodes on the surface of the unit (e.g. titanium alloy rings), ideally self drying and coated with a hydrophobic nanocoating. This would allow for rapid, high efficiency charging when the electrodes are brought into contact with an external power source (255).

In some embodiments, the battery may be an 80 mAh (milliamp-hour) solid state lithium battery, supplemented by a super capacitor (such as a 20 Microfarad super capacitor) as desired.

Other magnetic charging embodiments: Note that in some embodiments, if the user is willing to sleep with an induction coil mounted near the outside of the user's mouth, then the battery may be dispensed with, and instead the device may be powered either with a smaller rechargeable battery, or even directly via an induction coil.

Automated Device Configuration Embodiments

Although, as previously discussed, in some embodiments the device may be customized to fit a given user's mouth by manual methods, in other embodiments, it may be useful to automate this process.

Here in these embodiments, the process adjusting the adjustable mouthpiece device to fit at least some of the mouth, jaw, teeth, and lips of a human user can further comprise using a smartphone equipped with any of a video camera and a lidar sensor to acquire images of the user's open mouth and teeth.

Figure 17:
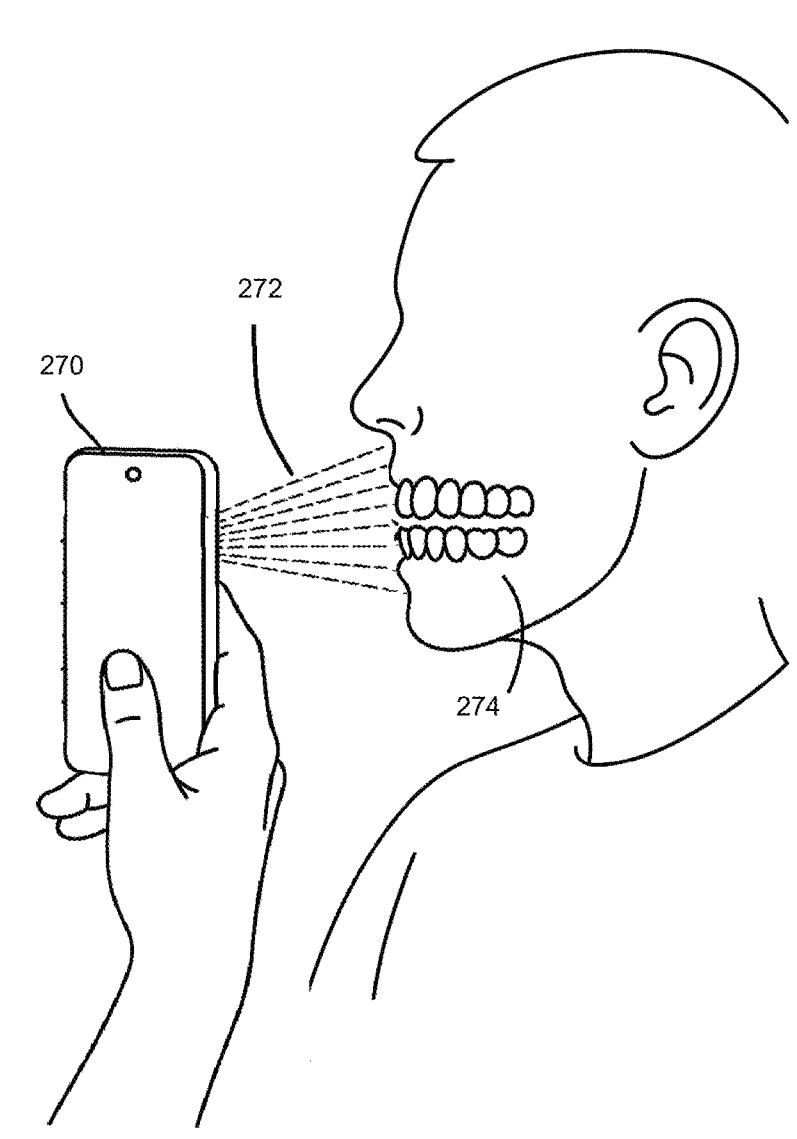
FIG. 17 shows an embodiment where a smartphone or other optical/lidar scanning device may be used to scan the user's mouth, and the information used to automatically construct user customized versions of the mouthpiece device.

FIG. 17 shows an embodiment where a smartphone or other optical/lidar scanning device may be used to scan the user's mouth, and the information used to automatically construct user customized versions of the mouthpiece device.

These images can then be assembled, usually by using a computer processor and suitable photogrammetry or 3D model generators to construct a 3D dimensional model of the user's mouth and teeth. Here, systems such as Canva AI 3D model maker, Meshy.ai, Adobe substance 3D sampler, can be used.

Once a suitable 3D image of the user's mouth and teeth are obtained, 3D models of the pivoting dental blocks may be automatically manipulated in order to determine what is are the optimum shapes for the pivoting dental blocks (110). Optimum shapes and positions of the archwires (150, 160) may also be determined.

These optimum pivoting dental block shapes can then be used, along with any of a 3D stereo lithography (SLA) or computer numerical control (CNC) machine, to construct user customized versions of at least some of the pivoting dental blocks, thus producing user customized pivoting dental blocks. In some embodiments, these customized pivoting dental blocks can be made from (comprise) dental LT clear resin, ethylene-vinyl acetate, or other material.

To expand on this, in this version of the invention, a custom-fitted dental device is produced using 3D scanning based on user-specific dental geometry. The scan is conducted with a standard smartphone (270) running a mobile application configured to guide the user through a photogrammetry process. The app instructs the user to capture a series of overlapping two-dimensional images of their teeth and mouth from multiple angles. The phone's camera records these images, and the data is uploaded to a processing module that uses photogrammetry algorithms to reconstruct a digital three-dimensional mesh. This method avoids the need for depth-sensing hardware or specialized intraoral scanners.

The scanning zone (272) represents the area in which the images are focused, extending from the smartphone (270) to the exposed region of the user's teeth (274). The photogrammetry system relies on image alignment, feature matching, and depth triangulation to determine spatial relationships between surfaces of the teeth. The result is a detailed mesh that digitally represents both upper and lower arches, including curvature and spacing between teeth.

This 3D mesh is imported into computer-aided design (CAD) software. Within the software, the dental device is virtually fitted to the contours of the scan. The geometry of the device can be adjusted to accommodate spacing, pressure points, and surface contact areas between upper and lower teeth. Once the design is finalized, the file is transferred to a 3D printer.

The device can be made using Dental LT Clear Resin, which is a Class IIa certified biocompatible material approved for long-term use in the mouth. It is printed using stereolithographic (SLA) 3D printing, which allows for accurate and detailed shapes. Dental LT Clear Resin is strong enough to hold its shape and fit securely between the teeth. After printing, the device is cleaned and finished following the resin manufacturer's instructions to make sure it is safe to use. The shape of the device is based on the 3D mesh created from photogrammetry, so it fits the user's teeth closely. This process avoids the need for messy dental molds or in-person scanning, while still making a custom-fit device.

The invention claimed is:

1. A method of using an adjustable mouthpiece device to facilitate breathing of a human user during sleep, said method comprising:

adjusting said adjustable mouthpiece device to fit into jaws of said human user, said adjustable mouthpiece device comprising:

two pivoting dental blocks configured to fit inside opposite sides of said jaw, said two pivoting dental blocks connected to each other by an upper archwire and a lower archwire, each of said upper and lower archwires comprising opposing ends;

each said upper and lower archwires having between 170-190 degrees of curvature so that said opposing ends fit inside said mouth;

a rechargeable battery, said rechargeable battery located between said two pivoting dental blocks;

each of said two pivoting dental blocks comprising gap-separated upper wire interface face and gap-separated lower wire interface face, gap-separated upper fastener face and gap-separated lower fastener face, upper tooth-accepting face and lower tooth-accepting face, thus creating a gap that separates at least said upper and lower wire interface faces;

each of said gap-separated upper and lower wire interface faces comprising a wire hole configured to admit one of said opposing ends;

wherein when said opposing ends are inserted into said wire holes, and fastened to said upper and lower wire interface faces, said upper archwire connects said upper wire interface faces of said two pivoting dental blocks, and said lower archwire connects said lower wire interface faces of said two pivoting dental blocks;

at least said upper archwire further configured with a lip opening fixture, positioned midway between said opposing ends, which is configured to extend outside of said jaw and past at least a middle portion of said lip, so that said lip is partially elevated above its normal resting state;

wherein said upper and lower tooth-accepting faces further comprise recesses configured to accommodate said user's teeth;

configuring said two pivoting dental blocks and said gaps to exert opposite torque forces on said upper and lower tooth-accepting faces such that said opposite torque forces are selected to be greater than a minimum amount needed to partially open said jaws, but less than a maximum amount needed to close said jaws against said opposite torque forces;

wherein said adjusting further comprise adjusting said lip opening fixture such that when said user's face is in a relaxed state, said opposite torque forces and said lip opening fixture enable said user to breathe through said mouth, and when said user activates their jaw muscles or lip muscles, said jaw muscles and lip muscles can overcome said torque forces and said lip opening fixture, thus enabling said user, while asleep, to close their lips and/or swallow saliva; and using at least one processor and at least one sensor to automatically monitor a physiological status of said human user during sleep.

2. The method of claim 1, wherein each of said two pivoting dental blocks comprise an upper portion and a lower portion, said portions connected by a mechanical pivot;

wherein said gap-separated upper wire interface face, gap-separated upper fastener face, and upper tooth-accepting face are positioned on said upper portion, and said gap-separated lower wire interface face, gap-separated lower fastener face, and lower tooth-accepting face are positioned on said lower portion;

wherein said at least one processor comprises at least one embedded mouthpiece processor;

wherein at least one of said upper and lower portions of at least one of said pivoting dental blocks further comprise said at least one embedded mouthpiece processor configured with a wireless Bluetooth Low Energy (BLE) transceiver.

3. The method of claim 2, wherein said mechanical pivot comprises any of a ball joint and at least one torque applying electronic actuator, and said at least one torque applying electronic actuator is configured to exert opposite torque forces on said upper and lower tooth-accepting faces.

4. The method of claim 1, wherein at least said upper archwire comprises an upper attachment device disposed midway between said opposite sides, and said lip opening fixture comprises at least one upper lip opening fixture configured to attach to at least one upper attachment device.

5. The method of claim 4, wherein said lower archwire comprises a lower attachment device disposed midway between said opposite sides, and said lip opening fixture comprises at least one lower lip opening fixture configured to attach to at least one lower attachment device.

6. The method of claim 4, wherein at least one of said upper lip opening fixture and a lower lip opening fixture further contain any of a lip opening spring or a lip opening electronic actuator configured to separate said user's lips while said lips are relaxed.

7. The method of claim 4, wherein said upper lip opening fixture and said lower opening further comprise an attached covering disposed between said upper lip opening fixture and a lower lip opening fixture, said attached covering configured to increase humidification of said user's mouth by retaining at least some moisture exhaled by said user.

8. The method of claim 7, wherein said attached covering comprises any of a woven or nonwoven fabric, fiber, hydrogel, or humidity absorbent polymer.

9. The method of claim 1, wherein said rechargeable battery further comprises an induction coil, further recharging said rechargeable battery by bringing an inductive charger proximate to said induction coil.

10. The method of claim 1, wherein each of said two pivoting dental blocks comprise a single portion of a block material partially bisected by a gap that divides said dental block into an upper portion and a lower portion on a front wire-facing side, and a single portion on an opposite side;

wherein said gap-separated upper wire interface face, gap-separated upper fastener face, and upper tooth-accepting face are positioned on said upper portion, and said gap-separated lower wire interface face, gap-separated lower fastener face, and lower tooth-accepting face are positioned on said lower portion;

said each of said two pivoting dental blocks comprise an elastic block material selected to be capable of repeatedly pivoting about said single portion.

11. The method of claim 1, wherein said lip opening fixture comprises at least one archwire fold, said archwire fold configured to protrude out of the middle of said mouth, and further bent at an upward angle so as to elevate at least the middle of said lips.

12. The method of claim 1, wherein each of said gap-separated upper and lower fastener faces comprises screw holes, each aligned perpendicular to said wire holes and in contact with said wire holes, and configured so that a screw inserted into said screw hole fastens said opposing ends of said archwires to said two pivoting dental blocks; and said adjusting further comprising altering any one of a length of said upper or lower archwire, altering a distance of which any of said upper or lower archwire opposing end enters any of said wire holes, and adjusting said upper and lower tooth-accepting faces so that said adjustable mouthpiece device fits into said mouth.

13. The method of claim 1, wherein said minimum amount is greater than 4 Newtons of force, and said maximum amount is less than 25 Newtons of force.

14. The method of claim 13, wherein said adjustable mouthpiece device further is configured to use at least one processor to control any of at least one torque applying electronic actuator or a lip opening electronic actuator.

15. The method of claim 1, wherein said at least one of said at least one sensor is embedded in said adjustable mouthpiece device, thus comprising at least one embedded mouthpiece sensor;

at least one of said at least one embedded mouthpiece sensor comprising any of a pulse oximeter, temperature sensor, airflow sensor or moisture sensor; and wherein said at least one embedded mouthpiece sensor is configured to transmit sensor readings to any of said at least one processor and a wireless transceiver.

16. The method of claim 1, wherein said at least one processor comprises an external processor;

said external processor is configured to receive data from said at least one sensor;

further using said external processor and said data to adjust a processor-controlled actuator to adjust any of said minimum amount and said maximal amount.

17. The method of claim 16, wherein said external processor comprises an external wrist-mounted computerized device;

said external computerized device comprising an external wireless transceiver;

said external processor configured to receive data from of an embedded mouthpiece sensor and a wrist-mounted computerized device sensor;

further using said external processor, said external wireless transceiver, and said data to adjust said processor-controlled actuator according to said data.

18. The method of claim 1, wherein adjusting said adjustable mouthpiece device to fit at least some of the mouth, jaw, teeth, and lips of said human user further comprises:

using a smartphone equipped with any of a video camera and a lidar sensor to acquire images of said user's open mouth and teeth;

using said images to construct a 3D dimensional model of said user's mouth and teeth;

and using said images, any of a 3D stereo lithography (SLA) or computer numerical control (CNC) machine to construct user customized versions of at least some of said pivoting dental blocks, thus producing user customized pivoting dental blocks.

19. The method of claim 18, wherein said customized pivoting dental blocks comprise dental LT clear resin, ethylene-vinyl acetate, or other material.

20. The method of claim 1, wherein at least one of said pivoting dental blocks further comprises at least two external electrodes configured to charge said rechargeable battery by direct contact to an external power source.

* * * * *